United States Patent [19]

DeHaven-Hudkins et al.

[11] Patent Number: 5,290,796

[45] Date of Patent: Mar. 1, 1994

[54] SUBSTITUTED 3-PIPERIDINEALKANAMINES AND ALKANAMIDES AND COMPOSITIONS AND METHOD OF USE THEREOF

[75] Inventors: Diane L. DeHaven-Hudkins, Chester Springs, Pa.; John P. Mallamo, Kinderhook; William F. Michne, Poestenkill, both of N.Y.; Martha R. Heimann, Durham, N.C.

[73] Assignee: Sterling Winthrop Inc., New York, N.Y.

[21] Appl. No.: 979,714

[22] Filed: Nov. 20, 1992

[51] Int. Cl.$^5$ .................. A61K 31/445; C07D 211/32
[52] U.S. Cl. .................. 514/326; 514/212; 514/316; 514/331; 540/597; 546/186; 546/191; 546/207; 546/208; 546/209; 546/210; 546/211; 546/212; 546/214; 546/223; 546/229; 546/246; 546/247; 546/233; 546/234
[58] Field of Search ............... 540/597; 546/186, 191, 546/194, 207, 208, 209, 210, 211, 212, 214, 223, 229, 246, 247, 233, 234; 514/212, 316, 326, 331

[56]  References Cited
U.S. PATENT DOCUMENTS

| | | | |
|---|---|---|---|
| 3,342,826 | 9/1967 | Miller | 546/233 |
| 3,431,267 | 3/1969 | Welcher | 546/246 |
| 3,879,399 | 4/1975 | Zondler | 546/246 |
| 4,931,436 | 6/1990 | Zugel | 514/220 |
| 5,023,266 | 6/1991 | Langer et al. | 514/317 |

FOREIGN PATENT DOCUMENTS

| | | |
|---|---|---|
| 449187 | 10/1991 | European Pat. Off. |
| 445195 | 11/1991 | European Pat. Off. |
| 5069563 | 11/1978 | Japan .................. 546/233 |

OTHER PUBLICATIONS

Zymalkowski et al "Synthesis of Pyridine Derivatives" CA 56:2416h (1962).
Loew, et al., Endog. Exog. Opiate Agonists and Antagonists, E. L. Way, editor, Pergamon: Elmsford, N.Y. 1980, pp. 39–42.
Glennon, et al., J. Med. Chem. 1991, 34, 3360–3365.

*Primary Examiner*—C. Warren Ivy
*Assistant Examiner*—Celia Chang
*Attorney, Agent, or Firm*—Michael D. Alexander; Paul E. Dupont

[57]  ABSTRACT

The invention is related to compounds, being useful in treating psychosis, of the formula:

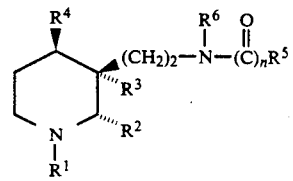

wherein
  $R^1$ is lower-alkyl, or phenyl-lower-alkyl;
  $R^2$, $R^3$ and $R^4$ are the same or different lower-alkyl;
  n is zero or one;
  $R^5$ is hydrogen, lower-alkyl, $C_3$–$C_7$-monocyclic cycloalkyl, lower-alkoxy, phenyl, phenyl-lower-alkyl, phenyl-lower-alkyl in which the phenyl ring is substituted in the 2, 3, or 4-position by one to two, the same or different, halogen substituents, or $R^5$ is a 5-membered aromatic monocyclic heterocycle selected from the group consisting of thienyl, furanyl and isoxazolyl;
  $R^6$ is hydrogen or lower-alkyl; or when n is zero, $R^5$ and $R^6$ together are —$(CH_2)_m$— wherein m is an integer from four to six; with the proviso that when $R^1$, $R^2$, $R^3$ and $R^4$ are methyl, n is zero and $R^6$ is hydrogen or methyl, $R^5$ cannot be hydrogen; further provided that when n is zero, $R^5$ cannot be lower-alkoxy, phenyl, or a 5-membered aromatic monocyclic heterocycle, or a pharmaceutically acceptable acid-addition salt thereof.

16 Claims, No Drawings

SUBSTITUTED 3-PIPERIDINEALKANAMINES AND ALKANAMIDES AND COMPOSITIONS AND METHOD OF USE THEREOF

BACKGROUND OF THE INVENTION (a) Field of the Invention

The invention relates to novel 3-piperidinealkanamines and alkanamides, to compositions containing the same, and to the method of use thereof in the treatment of central nervous system disorders.

A number of know antipsychotic drugs are disclosed in the art which have been shown to share a selective, high affinity for sigma receptors, which are sites where psychotomimetic opiates, such as (+)-pentazocine and N-allylnormetazocine, act. It has been suggested that the antipsychotic behavioral profile of these antipsychotic drugs can be attributed to their role as competitive antagonists of sigma receptor binding and that a systematic screen for drugs that block sigma receptors may provide a valuable strategy for identifying novel antipsychotic agents. Additionally, it has been shown that the relative potencies of these agents studied in vivo correspond well with their relative binding affinities obtained in vitro. See, for example, Synder and Largent, J. Neuropsychiatry 1989, 1 (1), 7–15; Largent, et al., Eur. J. Pharmacol. 1988, 155, 345–347; Deutsch, et al., Clinical Neuropharmacology 1988, 11(2), 105–119; Tayler, et al., Drug Development Research 1987, 11, 65–70; Ferris, et al., Life Sciences 38(25), 2329–2337; and Su, et al., Neuroscience Letters 1986, 71, 224–228.

(b) Information Disclosure Statement

Welcher, U.S. Pat. No. 3,431,267, issued Mar. 4, 1969, discloses 2,3-dimethyl-3-piperidinepropanamine

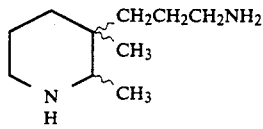

as a fungicide and pesticide.

Loew, et al., Endog. Exog. Opiate Agonists and Antagonists, E. L. Way, editor, Pergamon: Elmsford, New York 1980, pp 39–42, disclose 1-$R_1$-2,3,4,4-tetramethylpiperadines of general formula

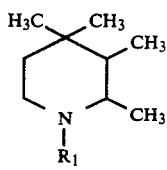

wherein $R_1$ is 3-furanylmethyl, 2-furanylmethyl, 2-propenyl, cyclopropylmethyl, phenylethyl, methyl and hydrogen without an indication of utility.

Langer, et al., U.S. Pat. No. 5,023,266, issued Jun. 11, 1991, disclose compounds of the formula:

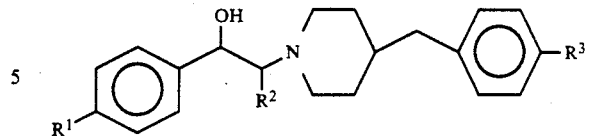

wherein:
$R^1$ denotes a halogen atom or a hydroxy group;
$R^2$ denotes a hydrogen atom or a methyl group; and
$R^3$ denotes a hydrogen or halogen atom.

The compounds are said to be useful in the treatment of phychotic disorders.

Gray and Cheng, European Patent Application 445195, published Nov. 6, 1991, disclose a series of ethanobicyclic amine derivatives which are said to be useful in the treatment of CNS disorders such as psychotic disorders, convulsions, dystonia and cerebral ischemia.

Cain, et al., European Patent Application 449187, published Oct. 2, 1991, disclose a series of disubstituted piperidine ether derivatives which are said to be useful in treating physiological or drug induced psychosis or dyskinesia in mammals or fungal disease in plants.

Glennon, et al., J. Med. Chem. 1991. 34, 3360–3365, disclose a series of novel 4-phenylpiperidine derivatives which are stated to bind with high affinity to sigma receptors.

SUMMARY OF THE INVENTION

The invention relates to a compound of Formula I:

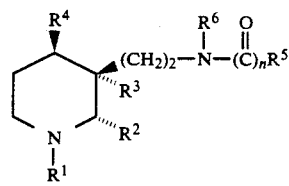

wherein:
$R^1$ is lower-alkyl, or phenyl-lower-alkyl;
$R^2$, $R^3$ and $R^4$ are the same or different lower-alkyl;
n is zero or one;
$R^5$ is hydrogen, lower-alkyl, cycloalkyl, lower-alkoxy, phenyl, phenyl-lower-alkyl, phenyl-lower-alkyl in which the phenyl ring is substituted in the 2, 3, or 4-position by one to two, the same or different, halogen substituents, or $R^5$ is a 5-membered aromatic monocyclic heterocycle containing from one to two heteroatoms selected from the group consisting of oxygen, nitrogen and sulfur; and
$R^6$ is hydrogen or lower-alkyl; or when n is zero, $R^5$ and $R^6$ together are —$(CH_2)_m$— wherein m is an integer from four to six;
or a pharmaceutically acceptable acid-addition salt thereof; with the proviso that when $R^1$, $R^2$, $R^3$ and $R^4$ are methyl, n is zero and $R^6$ is hydrogen or methyl, $R^5$ cannot be hydrogen; further provided that when n is zero, $R^5$ cannot be lower-alkoxy, phenyl, or a 5-membered aromatic monocyclic heterocycle.

The compounds of the present invention bind with high affinity to sigma receptors and are thus useful in the treatment of central nervous system disorders.

Preferred compounds of Formula I above are those wherein:

$R^1$ is lower-alkyl;

$R^2$, $R^3$ and $R^4$ are the same lower-alkyl;

n is one;

$R^5$ is lower-alkoxy, phenyl-lower-alkyl in which the phenyl ring is substituted in the 2, 3, or 4-position by one or two chlorine substituents, or $R^5$ is a 5-membered aromatic monocyclic heterocycle containing one heteroatom selected from the group consisting of oxygen and sulfur; and $R^6$ is hydrogen or lower-alkyl.

Particularly preferred compounds of Formula I above are those wherein:

$R^1$, $R^2$, $R^3$ and $R^4$ are methyl;

n is one;

$R^5$ is lower-alkoxy, 3,4-dichlorophenyl-lower-alkyl or thienyl; and $R^6$ is hydrogen or methyl.

The invention further relates to pharmaceutical compositions which comprise a compound of Formula I together with a pharmaceutically acceptable carrier, adjuvant, diluent or vehicle.

The invention further relates to a method for the treatment of central nervous system disorders, especially psychoses, which comprises administering to a patient in need of such treatment an effective amount of a compound of Formula I.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec-butyl and the like.

The term lower-alkoxy as used herein means linear or branched alkyloxy substituents having one to about four carbon atoms and thus includes methoxy, ethoxy, propoxy, isopropoxy, butoxy, sec-butoxy and the like.

The term cycloalkyl as used herein means monocyclic hydrocarbon ring systems having three to about seven carbon atoms and thus includes cyclopropyl, cyclobutyl, cyclopentyl, cyclohexyl and cycloheptyl.

The term halogen, halo or halide as used herein means bromine, chlorine, iodine or fluorine.

The sythesis of compounds of the invention wherein n is zero and $R^5$ and $R^6$ are hydrogen may be outlined as shown in Scheme A:

Scheme A

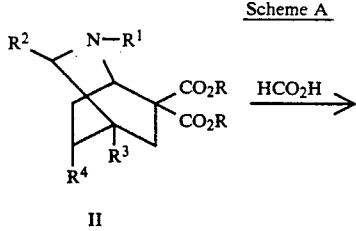

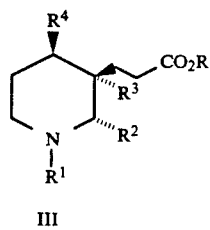

A suitably substituted dilower-alkyl 2-azabicyclo[2.2.2]octane-6,6-dicarboxylate (II, R=lower alkyl), preferably an ethyl ester, is treated with an excess of formic acid, and an excess of a base, preferably triethylamine in the absence of a solvent, at a temperature in the range of from about 110° C. up to about 160° C. to produce a lower-alkyl 3-piperidinepropanoate of the Formula III. Treatment of the lower-alkyl 3-piperidineproponoate of Formula III with an excess of sodium azide (NaN₃), in an acidic solvent, e.g. concentrated sulfuric acid, at a temperature in the range of from about 50° C. up to about 70° C. affords the compounds of Formula I wherein n is zero and $R^5$ and $R^6$ are hydrogen.

The compounds of Formula I wherein n is zero, $R^6$ is hydrogen and $R^5$ is cycloalkyl may be synthesized as shown in Scheme B:

Scheme B

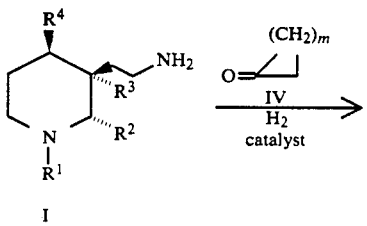

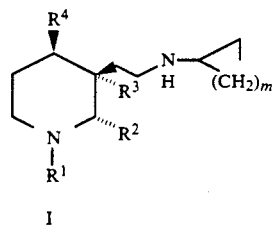

A compound of Formula I wherein n is zero and $R^5$ and $R^6$ are hydrogen is treated with one equivalent of an appropriate cycloalkanone of Formula IV wherein m is an integer from one to five, in an alcoholic solvent, e.g. ethanol, in the presence of a hydrogenation catalyst, e.g. palladium on carbon, on a Parr hydrogenator at a hydrogen pressure of about 50 psi.

The compounds of Formula I wherein n is zero, $R^6$ is hydrogen and $R^5$ is lower-alkyl, phenyl-lower-alkyl or substituted phenyl-lower-alkyl may be synthesized as shown in Scheme C:

Scheme C

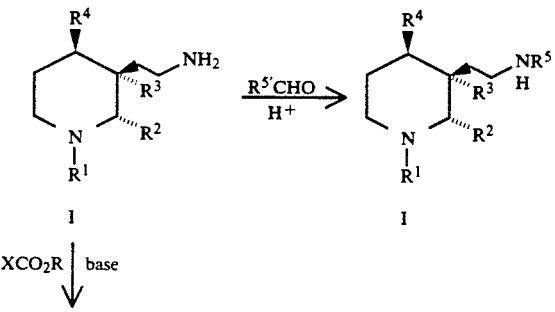

-continued
Scheme C

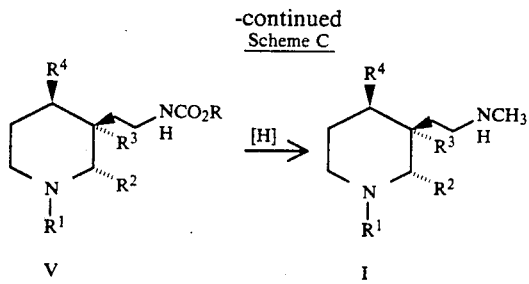

A compound of Formula I wherein n is zero and $R^5$ and $R^6$ are hydrogen is treated with one equivalent of an appropriate aldehyde, $R^{5'}$ CHO wherein $R^{5'}$ CHO is the corresponding aldehyde of the $R^5$ radical, for example, when the desired $R^5$ radical is $PhCH_2$ the corresponding aldehyde is PhCHO and when the desired $R^5$ radical is $CH_3$ the corresponding aldehyde is HCHO, in formic acid, at a temperature of about 100° C. to produce the corresponding compound of Formula I wherein n is zero, $R^6$ is hydrogen and $R^5$ is lower-alkyl, phenyl-lower-alkyl or substituted phenyl-lower-alkyl. Alternatively, when a compound of the Formula I is desired wherein n is zero, $R^6$ is hydrogen and $R^5$ is methyl, a compound of Formula I wherein n is zero and $R^5$ and $R^6$ are hydrogen can be treated with an excess of a lower-alkylhaloformate, $XCO_2R$ wherein X is a halogen, preferably chlorine, and R is lower-alkyl, in the presence of an excess of a base, preferably triethylamine, in a halogenated solvent, such as dichloromethane, at a temperature in the range of about 0° C. up to about 25° C. to produce a lower-alkyl carbamate of Formula V. This derivative can then be treated with an excess of a reducing agent, e.g. lithium aluminum hydride, in a solvent, such as tetrahydrofuran, at a temperature in the range of about 0° C. up to the boiling point of the solvent used to produce a compound of Formula I wherein n is zero, $R^6$ is hydrogen and $R^5$ is methyl. It will be understood that the above described methods for the preparation of compounds of Formula I wherein n is zero, $R^6$ is hydrogen and $R^5$ is lower-alkyl are equivalent to describing methods for the preparation of compounds of the Formula I wherein n is zero, $R^6$ is lower-alkyl and $R^5$ is hydrogen.

In those instances wherein it is desirable to prepare a compound of Formula I where n is zero, $R^6$ is lower-alkyl and $R^5$ is other than hydrogen it is convenient to proceed as shown in Scheme D:

Scheme D

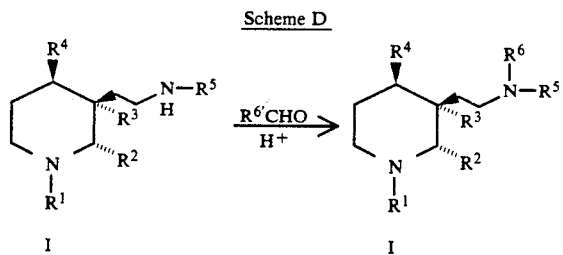

A compound of the Formula I wherein n is zero, $R^6$ is hydrogen and $R^5$ is other than hydrogen can be treated with one equivalent of an appropriate aldehyde, $R^{6'}$ CHO wherein $R^{6'}$ CHO is the corresponding aldehyde of the $R^6$ radical, for example, when the desired $R^6$ radical is $CH_3$ the corresponding aldehyde is HCHO, in formic acid, at a temperature of about 100° C. Alternatively, if a compound of Formula I wherein n is zero and $R^5$ and $R^6$ are the same lower-alkyl group is desired it is convenient to treat a compound of the Formula I wherein n is zero and $R^5$ and $R^6$ are hydrogen with at least two molar equivalents of an appropriate aldehyde, $R^{6'}$ CHO wherein $R'$CHO is as defined above, in formic acid, at a temperature of about 100° C. to produce the compounds of Formula I wherein n is zero and $R^5 = R^6 =$ lower-alkyl.

The compounds of Formula I wherein n is zero and $R^5$ and $R^6$ together are $—(CH_2)_m—$, wherein m is an integer from four to six, are prepared as shown in Scheme E:

Scheme E

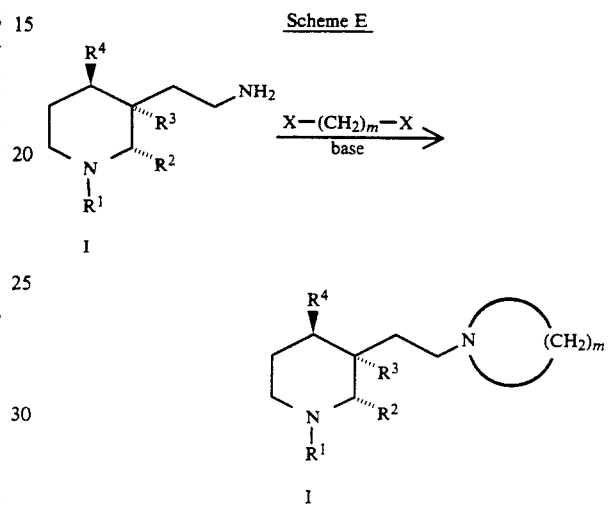

A compound of Formula I wherein n is zero and $R^5$ and $R^6$ are hydrogen is treated with an excess of a dihalide of formula $X—(CH_2)_m—X$ wherein X is a halide, preferably a bromide, in a suitable solvent, such as acetonitrile, in the presence of an excess of a base, such as potassium carbonate, at a temperature of about room temperature.

The compounds of Formula I wherein n is one may be synthesized as shown in Scheme F:

Scheme F

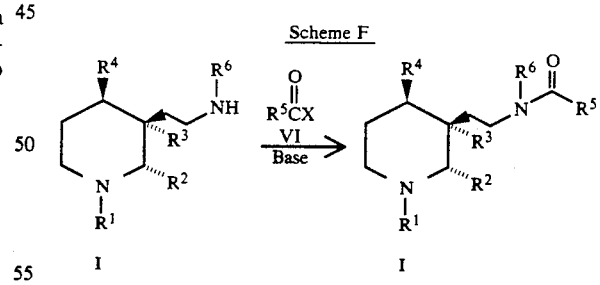

A compound of Formula I wherein n is zero, $R^5$ is hydrogen and $R^6$ is hydrogen or lower-alkyl is treated with an excess of an appropriate acylating agent of Formula VI, e.g. an acid halide or a haloformate, preferably an acid chloride or a chloroformate, in the presence of an excess of a base, preferably triethylamine, in a halogenated solvent, such as dichloromethane, at a temperature in the range of about −25° C. up to about 25° C., optionally in the presence of an acylation catalyst, e.g. 4-dimethylaminopyridine, to afford a compound of the Formula I wherein n is one and $R^6$ is hydrogen or lower-alkyl.

The dilower-alkyl 2-azabicyclo[2.2.2]octane-6,6-dicarboxylates of Formula II required for the synthesis of the compounds of Formula I are prepared as shown in Scheme G:

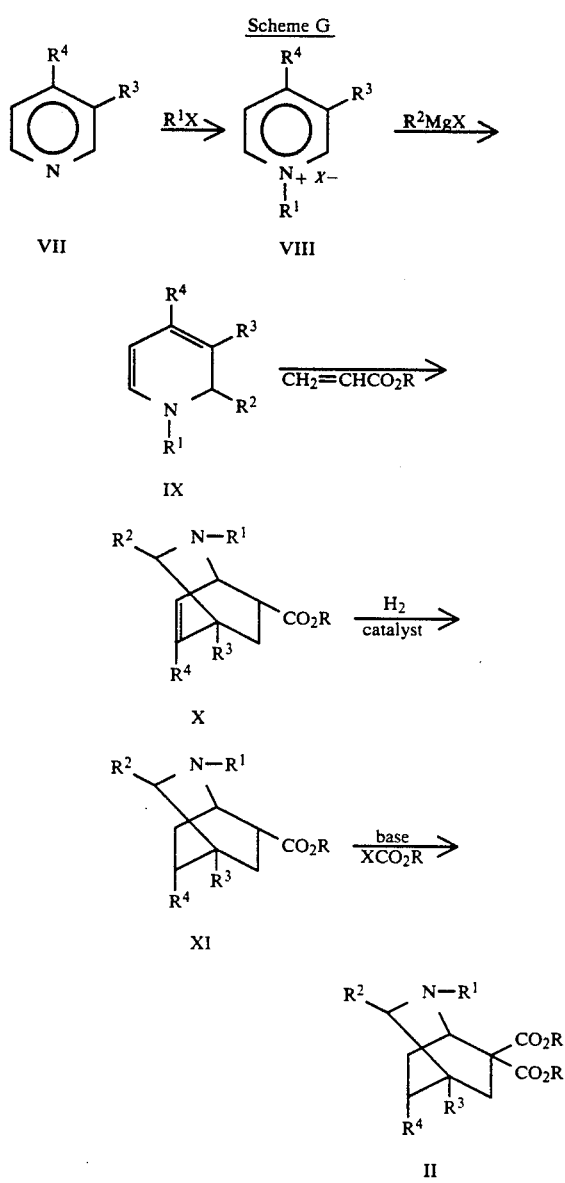

A suitably substituted pyridine derivative VII is treated with an appropriate alkylating agent, $R^1S$, in an alcoholic solvent, e.g. isopropanol, at a temperature in the range of from about 25° C. up to the boiling point of the solvent used to afford a pyridinium salt of the Formula VIII. The pyridinium salt is treated with an excess of an appropriate Grignard reagent, $R^2MgX$, in a solvent such as ether, at a temperature in the range of from about 0° C. up to about 25° C. to afford a 1,2-dihydropyridine of Formula IX. The 1,2-dihydropyridine (Iv) is then treated with a suitable lower-alkyl acrylate, $CH_2=CHCO_2R$, in a solvent such as toluene, at a temperature from about 25° C. up to the boiling point of the solvent used to afford a lower-alkyl 2-azabicyclo[2.2.2]oct-7-ene-6-carboxylate of Formula X. The compound of Formula X or acid-addition salt thereof, e.g. the hydrochloride, is hydrogenated at a hydrogen pressure of from about 15 psi to about 50 psi, in the presence of a catalyst, preferably palladium on carbon, in an alcoholic solvent, e.g. methanol or ethanol to afford the lower-alkyl 2-azabicyclo[2.2.2]octane-6-carboxylate of Formula XI. The compound of Formula XI is then treated with an excess of a base, preferably lithium diisopropylamide, followed by treatment with an excess of an appropriate lower-alkyl haloformate, $XCO_2R$, preferably a chloroformate, in a solvent such as tetrahydrofuran, at a temperature in the range of from about $-78°$ C. up to about 25° C. to afford the dilower-alkyl 2-azabicyclo[2.2.2]octane-6,6-dicarboxylates of Formula II.

In those instances wherein a compound of the Formula X is used in which $R^1$ is benzyl, debenzylation also occurs under the hydrogenation reaction conditions described in Scheme G to produce a compound of the Formula XI wherein $R^1$ is hydrogen. An appropriate $R^1$ substituent can be reintroduced into the compounds of Formula XI by treating the compound of Formula XI or acid-addition salt thereof, e.g. the hydrochloride, wherein $R^1$ is hydrogen with (a) an excess of formaldehyde and an excess of a base, preferably triethylamine, in an alcoholic solvent, e.g. ethanol, in the presence of about 15 psi to about 50 psi of hydrogen pressure on a Parr hydrogenator to afford a compound of Formula XI wherein $R^1$ is methyl; or (b) an excess of an appropriate alkylating agent, $R^1X$, in the presence of an excess of a base, such as potassium carbonate, in a solvent such as acetonitrile, at a temperature in the range of from about 25.C up to the boiling point of the solvent used.

The appropriately substituted cycloalkanone (IV), aldehyde ($R^5CHO$), lower-alkylhaloformate ($XCO_2R$), aldehyde ($R^6CHO$), acylating agent (VI), alkylating agent ($R^1X$), Grignard reagent ($R^2MgX$), and lower-alkylacrylate ($CH_2=CHCO_2R$) are either commercially available or can be prepared by procedures well known in the art.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, is precipitated with a second organic solvent or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC).

The following examples will further illustrate the invention without, however, limiting it thereto. The abbreviation NaOH stands for sodium hydroxide, MgSO$_4$ stands for magnesium sulfate, HCl stands for hydrochloric acid, NH$_4$OH stands for ammonium hydroxide, THF stands for tetrahydrofuran, Na$_2$SO$_4$ stands for sodium sulfate and NaHCO$_3$ stands for sodium bicarbonate.

Preparation of Starting Materials

Preparation 1

(a)

A mixture of 3,4-lutidine (112 mL, 1.0 mole), benzyl chloride (115 mL, 1.0 mole) and isopropanol (500 mL) was refluxed under nitrogen for 5 hours and then was stirred at room temperature for 60 hours. The mixture was diluted with ether and the resulting white precipitate was filtered and dried to afford 178.3 g (76%) of N-(phenylmethyl)-3,4-dimethylpyridinium chloride.

(b)

A solution of methyl iodide (112 mL, 1.8 mole) in ether (225 mL) was added dropwise to a suspension of magnesium turnings (44 g, 1.8 mole) in ether (225 mL) under nitrogen over a period of 1 hour. The mixture was stirred at room temperature for 1 hour, transferred into a 1000 mL addition funnel and then was added to a suspension of N-(phenylmethyl)-3,4-dimethylpyridinium chloride (350.7 g, 1.5 mole) in ether (1500 mL) under a nitrogen atmosphere. The reaction mixture was stirred at room temperature for 24 hours and was then poured into a solution of saturated ammonium chloride (3 L). The organic layer was separated and the aqueous layer was extracted with ether (1000 mL). The combined ether layers were washed with water (500 mL), then brine (500 mL) and were dried over sodium sulfate and potassium carbonate. The solvent was removed in vacuo to afford 284.1 g (76%) of 1,2-dihydro-N-(phenylmethyl)-2,3,4-trimethylpyridine as an amber oil.

(C)

A solution of 1,2-dihydro-N-(pheylmethyl)-2,3,4-trimethylpyridine (284.1 g, 1.14 mole) in toluene (3000 mL) under nitrogen was treated with ethyl acrylate (162 mL, 1.5 mole). The mixture was refluxed for 21 hours and the solvent was removed in vacuo. The residue was dissolved in ethanol (300 mL), treated with 10 N ethanolic HCl and diluted with ether. A precipitate formed, which was collected by filtration and recrystallized from ethanol (150 mL)/ether (1400 mL) to afford 117.5 g (22%) of ethyl 3,4,8-trimethyl-2-(phenylmethyl)-2-azabicyclo[2.2.2]-oct-7-ene-6-carboxylate hydrochloride as a white powder, m.p. 184°–186° C. The mother liquor from the above recrystallization was treated with concentrated ammonium hydroxide (30 mL) and water (500 mL). The organic layer was separated, washed with brine and dried over potassium carbonate. The solvent was removed in vacuo and the residue was purified by column chromatography on silica eluting with ethyl acetate/hexane (25/75). The residue was dissolved in ethanol (50 mL), treated with 10.5 N ethanolic HCl (10 mL) and diluted with ether (1200 mL). The product was collected by filtration and recrystallized from ethanol/ether to afford an additional 131.2 g of the product for a total yield of 47%.

(d)

A mixture of ethyl 3,4,8-trimethyl-2-(phenylmethyl)-2-azabicyclo[2.2.2]-oct-7-ene-6-carboxylate hydrochloride (17.4 g, 49.7 mol), 10% palladium on carbon (1.7 g) and ethanol (200 mL) was hydrogenated on a Parr hydrogenator at 50 psi for 6 hours. The mixture was removed from the Parr hydrogenator, cooled to 0° C. and triethylamine (7.0 mL, 50 mmol), followed by 37% formaldehyde (4.1 mL, 55 mmol) were added The mixture was then placed back on the Parr hydrogenator at 50 psi for 1 hour. The reaction mixture was removed from the Parr hydrogenator, the catalyst was removed by filtration and the solvent was removed in vacuo. The residue was dissolved in water, basified with concentrated ammonium hydroxide (20 mL) and extracted with ether (3×300 mL). The combined organic layers were washed with brine (50 mL), dried over potassium carbonate and concentrated in vacuo to afford 11.5 g (96%) of ethyl 2,3,4,8-tetramethyl-2-azabicyclo[2.2.2]-octane-6-carboxylate as a pale yellow oil.

(e)

To a solution of diisopropylamine (3.0 mL, 22 mmol) in THF (34 mL) at 0° C. under nitrogen was added n-BuLi (8.8 mL, 22 mmol, 2.5M in hexanes). A solution of ethyl 2,3,4,8-tetra-methyl-2-azabicyclo[2.2.2]octane-6-carboxylate (4.8 g, 20 mmol) in THF (46 mL) was added to the mixture and the reaction was stirred at 0° C. for 1 hour. Ethyl chloroformate (2.3 mL, 24 mmol) in THF (3 mL) was then added and the mixture was stirred for 15 minutes. The reaction mixture was diluted with saturated sodium chloride and partitioned between water and ether. The aqueous layer was extracted with ether (2X) and the combined organic layers were dried over anhydrous MgSO$_4$. The solvent was removed in vacuo and the residue was purified by column chromatography on silica eluting with ether/hexanes (15/85) to afford 3.9 g (63%) of diethyl 2,3,4,8-tetramethyl-2-azabicyclo[2.2.2]octane-6,6-dicarboxylate as a yellow oil.

Preparation 2

(a)

A mixture of ethyl 3,4,8-trimethyl-2-(phenylmethyl)-2-azabicyclo[2.2.2]-oct-7-ene-6-carboxylate hydrochloride (26.2 g, 75 mmol), 10% palladium on carbon (2.6 g) and ethanol (200 mL) were placed on a Parr hydrogenator at 50 psi for 3.5 hours. The catalyst was removed by filtration and the solvent was removed in vacuo to afford crude ethyl 3,4,8-trimethyl-2-azabicyclo[2.2.2-octane-6-carboxylate hydrochloride as a yellow oil, which was used directly in the next step.

(b)

A mixture of the above crude product (approximately 75 mmol), potassium carbonate (104 g, 0.75 mol), benzyl chloride (8.6 mL, 75 mmol) and acetonitrile (500 mL) were refluxed under nitrogen for 24 hours. The reaction mixture was filtered and the solvent was removed in vacuo to afford 22.4 g (93%) 3,4,8-trimethyl-2-(phenylmethyl)-2-azabicyclo[2.2.2]octane-6-carboxylate as a golden oil.

(c)

To a solution of diisopropylamine (13.2 mL, 94 mmol) in THF (175 mL) at −60° C. under nitrogen was added n-BuLi (36.2 mL, 94 mmol, 2.6M hexane). The mixture was stirred for 30 minutes, cooled to −78° C. and ethyl 3,4,8-trimethyl-2-(phenylmethyl)-2-azabicyclo[2.2.2]octane-6-carboxylate (26.8 g, 85 mmol) in THF (225 mL) was added. The mixture was stirred for 3 hours, then ethyl chloroformate (8.96 mL, 94 mmol) in THF (20 mL) was added dropwise. The mixture was stirred for 24 hours, quenched with saturated NH4Cl, and poured into water (1000 mL). The solution was extracted with ether (3X), and the organic layers were combined and dried over MgSO4. The ether layer was treated with charcoal and the solvent was removed in vacuo to afford 32.1 g (97%) of diethyl 3,4,8-trimethyl-2-(phenylmethyl)-2-azabicyclo-[2.2.2]octane-6,6-dicarboxylate as a golden oil.

Preparation 3

By a substantially similar process to that described in Preparation 1a-e it is contemplated that diethyl 2,3,4trimethyl-8-ethyl-2-azabicyclo[2.2.2]octane-6,6-dicarboxylate and diethyl 3,8-diethyl-2,4-dimethyl-2-azabicyclo[2.2.2]octane-6,6-dicarboxylate can be prepared from 4-ethyl-3-methylpyridine and the appropriate Grignard reagent.

Preparation of Final Products (a)

To diethyl 2,3,4,8-tetramethyl-2-azabicyclo[2.2.2]octane-6,6-dicarboxylate (121 g, 389 mmol) at 0° C. was added formic acid (121 mL, 3.2 mol), followed by triethylamine (179 mL, 1.3 mol). The mixture was slowly heated to 160° C. over a period of 2 hours and was stirred at 160° C. for 20 minutes. The mixture was cooled to room temperature, and allowed to stand under nitrogen for 24 hours. The mixture was basified by the addition of saturated NaHCO3 and was extracted with ether (3X). The organic layers were combined, washed with saturated NaHCO3 then brine and were dried over anhydrous MgSO4. The solvent was removed in vacuo and the residue was taken up in 0.5N HCl (500 mL) and washed with hexane (3X). The aqueous layer was basified with concentrated NH4OH and extracted with ether (3X). The ether layer was dried over MgSO4 and concentrated in vacuo to afford 34 g (36%) of ethyl 1,2,3,4-tetramethyl-3-piperidinepropanoate as a yellow oil. The combined aqueous phases were concentrated in vacuo and the residue was triturated with hot ethanol (800 mL at 70° C.). The solution was filtered, triturated with additional hot ethanol (300 mL) and filtered once again. The ethanol filtrates were combined, acidified with concentrated H2SO4 and refluxed for 24 hours under nitrogen. The solution was basified with concentrated NH4OH and extracted with ether (3X). The ether layers were combined, washed with saturated NaHCO3 (2X) and dried over MgSO4. The solvent was removed in vacuo to afford 28.5 g of additional product for a total yield of 62.5 g (67%). The product was treated with p-toluenesulfonic acid to afford ethyl 1,2,3,4-tetramethyl-3-piperidinepropanoate-4-methylbenzenesulfonate as a white powder, m.p. 171-171.5.C.

(b)

Ethyl 1,2,3,4-tetramethyl-3-piperidinepropanoate (34.0 g, 141 mmol) was dissolved in concentrated sulfuric acid (300 mL) under a nitrogen atmosphere and the mixture was heated to 60° C. Sodium azide (18.35 g, 282 mmole) was then added in small portions (300–500 mg) over a three hour period at such a rate that a temperature range of 50°–70° C. was maintained. The mixture was then stirred at 60° C. for 2 hours, cooled to room temperature and poured onto ice-water (800 mL). The solution was basified with 35% NaOH and extracted with ether (3X). The organic layers were combined, dried over anhydrous MgSO4 and concentrated in vacuo to afford 18.5 g (71%) of 1,2,3,4-tetramethyl-3-piperidineethanamine as a yellow oil. The product was treated with ethereal HCl to afford the product as a dihydrochloride salt. The salt was isolated as a white powder and had a melting point of 233°–235° C.

(c)

A mixture of 1,2,3,4-tetramethyl-3-piperidineethanamine (2.0 g, 10.7 mmol), ethanol (50 mL), cyclopentanone (950 μL, 10.7 mmol) and 10% palladium on carbon (1.0 g) was placed on a Parr hydrogenator under 50 psi of hydrogen pressure for four hours. The reaction mixture was filtered to remove the catalyst and the solvent was removed in vacuo to afford 2.5 g (93%) of N-cyclopentyl-1,2,3,4-tetramethyl-3-piperidineethanamine as a yellow oil. The product was dissolved in ether/ethanol and treated with ethereal HCl to afford the product as a dihydrochloride hemihydrate. The dihydrochloride hemihydrate was isolated as a white powder and had a melting point of 201°–202.5° C.

EXAMPLE 2

(a)

A mixture of diethyl 3,4,8-trimethyl-2-(phenylmethyl)-2-azabicyclo[2.2.2]octane-6,6-dicarboxylate (3.4 g, 8.8 mmol) formic acid (3 mL) and triethylamine (4 mL) was heated to 160° C. for 1.5 hours. The reaction mixture was cooled to room temperature and allowed to stand for 24 hours. The mixture was basified with concentrated NH4OH and the mixture was extracted with ether (3X). The organic layers were combined, dried over anhydrous MgSO4 and concentrated in vacuo to afford 2.6 g (93%) of ethyl 2,3,4-trimethyl-1-(phenylmethyl)-3-piperidinepropanoate as a yellow oil.

(b)

Following a procedure substantially similar to that described in Example 1b, 1.3 g (76%) of 2,3,4-trimethyl-1-(phenylmethyl)-3-piperidineethanamine was obtained as a yellow oil from ethyl 2,3,4-trimethyl-1-(phenylmethyl)-3-piperidine-propanoate (2.04 g, 6.4 mmol), sodium azide (0.83 g, 12.8 mmol) and concentrated sulfuric acid (14 mL). The product was treated with ethereal HCl to afford the product as the hydrochloride salt. The salt was isolated as a white solid and had a melting point of 183°–185° C.

EXAMPLE 3

A mixture of N-cyclopentyl-1,2,3,4-tetramethyl-3-piperidineethanamine (13.0 g, 52 mmol), 37% formaldehyde (1.55 g, 52 mmol) and formic acid (70 mL) was heated to 100° C. for 3 hours and was then stirred at room temperature for 24 hours. The reaction mixture was basified with concentrated ammonium hydroxide (NH$_4$OH) and extracted with methylene chloride (3X). The organic layers were combined, dried over anhydrous MgSO$_4$ and concentrated in vacuo to afford 13.3 g (97%) of N-cyclopentyl-N-1,2,3,4-pentamethyl-3-piperidineethanamine as a yellow oil. The product was dissolved in ether/ethanol and treated with ethereal HCl to afford 2.8 g of the dihydrochloride salt as a white solid. The salt had a melting point of 212°–215° C.

Example 4

Following a procedure substantially similar to that described in Example 3, 1.0 g (45%) of N,N-1,2,3,4-hexamethyl-3-piperidineethanamine was obtained as a yellow oil from 1,2,3,4-tetramethyl-3-piperidineethanamine (1.9 g, 10.4 mmol), 37% formaldehyde (0.67 g, 22 mmol) and formic acid (10 mL). The product was treated with ethereal HCl to afford the product as a dihydrochloride hemihydrate salt. The salt was isolated as white crystals and had a melting point of 236.5°–237.5° C.

Example 5

A solution of 1,2,3,4-tetramethyl-3-piperidineethanamine (2.9 g, 16 mmol), triethylamine (10 mL) and methylene chloride (25 mL) was cooled to 0° C. and 3-thiophenecarboxylic acid chloride (2.3 g, 16 mmol) in methylene chloride (15 mL) was added. The reaction mixture was warmed to room temperature and stirred for 16 hours. The reaction mixture was diluted with ether (200 mL) and washed with saturated sodium bicarbonate (2×50 mL), water (50 mL), then brine (50 mL). The organic layer was separated, dried over Na$_2$SO$_4$ and treated with charcoal. The solvent was removed in vacuo and the residue was purified by column chromatography on silica eluting with ether (100%), then 2% diisopropylamine/ether, followed by 5% isopropylamine/ether to afford 2.9 g (62%) of N-[2-(1,2,3,4-tetramethyl-3-piperidinyl)-ethyl]-3-thiophenecarboxamide as an oil. The product was dissolved in ethanol (7 mL), cooled to 0° C., treated with 3.2N ethanolic HCl and diluted with ether to afford 3.1 g of the hydrochloride salt as a yellow solid. The salt was recrystallized from ethanol/ether and had a melting point of 228°–229° C.

Example 6

Following a procedure substantially similar to that described in Example 5, 38.1 g (76%) of ethyl-2-(1,2,3,4-tetramethyl-3-piperidinyl)ethyl carbamate was obtained as an oil from 1,2,3,4,-tetramethyl-3-piperidineethanamine (35.9 g, 195 mmol), triethylamine (70 mL), methylene chloride (325 mL) and ethyl chloroformate (23.9 g, 0.22 mol), after purification of the product by column chromatography on silica gel eluting with 5% ethyl acetate/hexane to 2% isopropylamine/15% ethyl acetate/hexane. 5.0 g Of the product was dissolved in ethanol (10 mL), cooled to 0° C. and treated with 7.2N ethereal HCl to afford 4.1 g of the hydrochloride salt as a white solid. The salt was recrystallized from ethanol/ether and had a melting point of 198°–200° C.

Example 7

(a)

A solution of ethyl 2-(1,2,3,4-tetramethyl-3-piperidinyl)ethyl carbamate (33.1 g, 118 mmol) in THF (350 mL) was cooled to 0° C. and lithium aluminum hydride (5.0 g, 132 mmol) was added in small portions over 15 minutes. The reaction mixture was warmed to room temperature, stirred for 3 hours, and then was refluxed for 16 hours. The reaction mixture was cooled to 0° C. and quenched with saturated Na$_2$SO$_4$ (25 mL). The mixture was stirred for 30 minutes and solid Na$_2$SO$_4$ (50 g) was added and the mixture was stirred for an additional 30 minutes. The aluminum salts were removed by filtration and the filtrate was concentrated in vacuo. The residue was purified by a Kugelrohr distillation at 80°–100° C. and 0.3 mm Hg to afford 20.5 g (87%) of N,1,2,3,4-pentamethyl-3-piperidineethanamine as a colorless oil.

(b)

A solution of N-1,2,3,4-pentamethyl-3-piperidineethanamine (4.0 g, 20 mmol), triethylamine (5.6 mL, 40 mmol) and methylene chloride (35 mL) was cooled to −23° C. and 3,4-dichlorophenylacetic acid chloride (5.0 g, 22.5 mmol) in methylene chloride (15 mL) was added dropwise over 1 hour. The reaction mixture was stirred at −23° C. for 3 hours, then at room temperature for 16 hours. Dimethylaminopyridine (100 mg) was added and the mixture was stirred for 6 hours. Additional 3,4-dichlorophenylacetic acid chloride (2.0 g) in methylene chloride (10 mL) was added and the mixture was stirred at room temperature for 16 hours. The reaction mixture was diluted with ether (150 mL) and washed with saturated NaHCO$_3$ (2×50 mL), then brine (50 mL). The organic layer was concentrated in vacuo and the residue was purified by column chromatography on silica gel eluting with 10% ether/hexane, then isopropylamine/ether/hexane (1/10/89), followed by two acid-base work-ups and additional column chromatography on silica gel eluting with 2% isopropylamine/hexane to afford 2.7 g (35%) of 3,4-dichloro-N-methyl-N-[2-(1,2,3,4-tetramethyl-3-piperidinyl)ethyl]benzeneacetamide as a golden oil. The product was dissolved in ether (50 mL), cooled to 0° C., treated with 6.5N ethereal HCl and diluted with ether to afford 2.4 g of the hydrochloride salt as a white powder, m.p. 163°–165° C.

Example 8

(a)

Following a procedure substantially similar to that described in Example 1, parts a and b, but substituting the appropriately substituted 2-azabicyclo[2.2.2]octane-6,6-dicarboxylate of preparation 3 for diethyl 2,3,4,8-tetramethyl-2-azabicyclo[2.2.2]octane-6,6-dicarboxylate it is contemplated that there can be prepared: 1,2,3-trimethyl-4-ethyl-3-piperidineethanamine and 1,3-dimethyl-2,4-diethyl-3-piperidineethanamine.

(b)

Following a procedure substantially similar to that described in Example 5, but substituting the appropriate acid halide for 3-thiophenecarboxylic acid chloride it is contemplated that the products of Example 5(a) can be converted into N-[2-(1,2,3-trimethyl-4-ethyl-3-piperidinyl)ethyl]benzeneacetamide and 2-chloro-N-[2-

(1,3-dimethyl-2,4-diethyl-3-piperidinyl)ethyl]-benzeneacetamide.

Example 9

Following a procedure substantially similar to that described in Example 5, but substituting the appropriate acid halide for 3-thiophenecarboxylic acid chloride it is contemplated that the following compounds can be prepared: N-[2-(1,2,3,4-tetramethyl-3-piperidinyl)ethyl]-2-furancarboxamide, N-[2-(1,2,2,3-tetramethyl-3-piperidinylethyl]-2-isoxazolecarboxamide and N-[2-(1,2,3,4-tetramethyl-3-piperidinyl)ethyl]benzamide.

Example 10

A solution of 1,2,3,4-tetramethyl-3-piperidineethanamine (9.8 g, 53 mmol) in acetonitrile (50 mL) was added dropwise over about 2 hours to a suspension of 1,4-dibromobutane (6.6 mL, 55.7 mmol) and potassium carbonate (26 g, 200 mmol) in acetonitrile (250 mL). The reaction mixture was stirred at room temperature for 24 hours, diluted with ether and the inorganic salts were removed by filtration. The solvent was removed in vacuo and the oily residue was purified by column chromatography on silica gel eluting with 2% isopropylamine/hexanes to afford 5.8 g (46%) of 1,2,3,4-tetramethyl-3-[2-(1-pyrrolidinyl)ethyl]piperidine. The product was dissolved in ether (25 mL) and treated with 6.5N ethereal HCl (10 mL) at 0° C. The mixture was warmed to room temperature, diluted with ether (10 mL) and cooled back to 0° C. to precipitate the dihydrochloride salt. The salt (4.3 g) was isolated as a white solid and had a melting point of 225°-227° C. (dec.) when recrystallized from ether (35 mL).

BIOLOGICAL TEST RESULTS

In standard biological test procedures, representative examples of the compounds of the invention have been found to bind with high affinity to sigma receptors, and are thus useful in the treatment of central nervous system disorders such as psychoses, dystonias, dyskinesias, Parkinson's syndrome, Huntington's chorea, Tourette syndrome and the like, especially psychoses, e.g. schizophrenic psychoses, manic depressive psychoses and the like.

The sigma receptor binding activity of representative compounds of the invention was demonstrated by following a procedure essentially as described by Hudkins and DeHaven-Hudkins, Life Sci. 1991. 49(17), 1229–1235.

Brain tissue was prepared from male Hartley guinea pigs (Hazelton Labs, Denver, Pa.) which were anesthetized with $CO_2$ and sacrificed by decapitation. All animal care and use procedures were in accord with the "Guide for the Care and Use of Laboratory Animals" (NIH Publ. No. 86-23, 1985). Homogenization was performed in 10 volumes (wt/vol) of 0.32M sucrose with a Brinkmann Polytron at setting 5, 30 sec. The homogenate was centrifuged at 900 x g for 10 min at 4° C., and the supernatant was collected and centrifuged at 22,000 x g for 20 min at 4° C. The pellet was resuspended in 10 volumes of Tris-HCl buffer (50 mM, pH 7.4), incubated at 37° C. for 30 min, and centrifuged at 22,000 x g for 20 min at 4° C. Following this, the pellet was resuspended in Tris buffer and frozen in 5–10 mL aliquots corresponding to a tissue concentration of 100 mg/mL, at −70° C. Binding characteristics of the membranes were stable for at least one month when stored at −70° C.

On the day of the assay, membrane aliquots were thawed, resuspended in fresh Tris-HCl buffer and stored on ice until use. Each assay tube contained 100 μL of [$^3$H]-(+)-pentazocine at a final concentration of approximately 0.5 nM or 100 μL of [$^3$H]di(2-tolyl)-guanidine (DTG) at a final concentration of approximately 4 nM, 100 μL of various concentrations of the compounds of interest, 500 μL of the tissue suspension and 300 μL of buffer to a final assay volume of 1 mL and a final tissue concentration of approximately 8 mg/tube, corresponding to approximately 0.15 mg protein/tube. Non-specific binding was defined by addition of a final concentration of 1 μM haloperidol to blank tubes for [$^3$H](+)-pentazocine assay or by addition of a final concentration of 10 μM haloperidol to blank tubes for [$^3$H]DTG assay. All tubes were incubated at 37° C. for 150 min in the [$^3$H](+)-pentazocine assay or at 25° C. for 90 min in the [$^3$H]DTG assay before termination of the reaction by rapid filtration over Whatman GF/B glass fiber filters that were presoaked in a solution of 0.5% polyethyleneimine for at least 1 hr prior to use. Filters were washed with three 4 ml volumes of cold Tris-HCl buffer.

Following addition of scintillation cocktail, samples were allowed to equilibrate for at least 4 hr. The amount of bound radioactivity was determined by liquid scintillation spectrometry using a Beckman LS 5000 TA liquid scintillation counter with an efficiency for tritium of approximately 60%. The results are reported as a percent (%) inhibition of binding at 10 μM.

Scatchard parameters and inhibition constants ($K_i$ values) for the binding of test compounds were also calculated using the EBDA/LIGAND program (McPherson, J Pharmacol. Meth. 1985, 14, 213–228), purchased from Elsevier/Biosoft, Inc. The $K_i$ values are expressed as the mean of at least two separate determinations performed in triplicate.

The following Table summarizes the results obtained from the testing of representative compounds of the invention.

TABLE 3

| Example No. | [$^3$H] (+)-Pentazocine | | [$^3$H]DTG | |
|---|---|---|---|---|
| | Percent Inhibition | Ki (nM) | Percent Inhibition | Ki (nM) |
| 1c | 57 | — | — | — |
| 3 | 90 | — | — | — |
| 2b | 83 | — | — | — |
| 4 | — | 23949 | 20 | — |
| 5 | 79 | — | — | — |
| 6 | 69 | — | — | — |
| 7b | 94 | — | — | — |
| 10 | — | 5980 | — | 7506 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

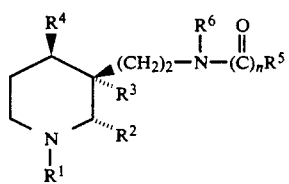

wherein:
$R^1$ is lower-alkyl, or phenyl-lower-alkyl;
$R^2$, $R^3$ and $R^4$ are the same or different lower-alkyl;
n is zero or one;
$R^5$ is hydrogen, lower-alkyl, $C_3$–$C_7$-monocyclic cycloalkyl, lower-alkoxy, phenyl, phenyl-lower-alkyl, phenyl-lower-alkyl in which the phenyl ring is substituted in the 2, 3, or 4-position by one to two, the same or different, halogen substituents, or $R^5$ is a 5-membered aromatic monocyclic heterocycle selected from the group consisting of thienyl, furanyl and isoxazolyl; and $R^6$ is hydrogen or lower-alkyl; or when n is zero, $R^5$ and $R^6$ together are —$(CH_2)_m$— wherein m is an integer from four to six; or a pharmaceutically acceptable acid-addition salt thereof; with the proviso that when $R^1$, $R^2$, $R^3$ and $R^4$ are methyl, n is zero and $R^6$ is hydrogen or methyl, $R^5$ cannot be hydrogen; further provided that when n is zero, $R^5$ cannot be lower-alkoxy, phenyl, or a 5-membered aromatic monocyclic heterocycle.

2. A compound according to claim 1 wherein $R^2$, $R^3$ and $R^4$ are the same lower-alkyl, n is zero; $R^5$ is hydrogen, lower-alkyl, or $C_3$–$C_7$-monocyclic cycloalkyl, and $R^5$ and $R^6$ are together —$(CH_2)_4$—.

3. A compound according to claim 2 wherein $R^2$, $R^3$ and $R^4$ are methyl.

4. A compound according to claim 3 wherein $R^1$ is methyl or benzyl and $R^6$ is hydrogen or methyl.

5. A compound according to claim 4 wherein $R^5$ is hydrogen or cyclopentyl.

6. A compound according to claim 1 wherein $R^2$, $R^3$ and $R^4$ are the same lower-alkyl; n is one; and $R^5$ is lower-alkoxy, phenyl-lower-alkyl in which the phenyl ring is substituted in the 2, 3, or 4-position by one to two, the same or different, halogen substituents, or $R^5$ is a 5-membered aromatic monocyclic heterocycle selected from the group consisting of thienyl, furanyl and isoxazolyl.

7. A compound according to claim 6 wherein $R^1$ is lower-alkyl; $R^2$, $R^3$ and $R^4$ are methyl; and $R^5$ is lower-alkoxy, phenyl-lower-alkyl in which the phenyl ring is substituted in the 2, 3, or 4-position by one or two chlorine substituents, or $R^5$ is a 5-membered aromatic monocyclic heterocycle containing one heteroatom selected from the group consisting of thienyl and furanyl.

8. A compound according to claim 7 wherein $R^1$ is methyl; $R^6$ is hydrogen or methyl; and $R^5$ is lower-alkoxy, 3,4-dichlorophenyl-lower-alkyl, or thienyl.

9. A compound according to claim 8 wherein $R^5$ is ethoxy, 3,4-dichlorophenylmethyl or 3-thienyl.

10. 3,4-Dichloro-N-methyl-N-[2-(1,2,3,4-tetramethyl-3-piperidinyl)ethyl]benzeneacetamide, or acid-addition salt thereof according to claim 9.

11. A pharmaceutical composition which comprises an antipsychotically effective amount of a compound of the formula:

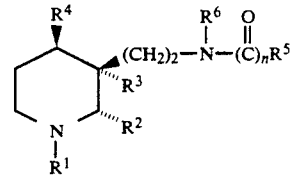

wherein
$R^1$ is lower-alkyl, or phenyl-lower-alkyl;
$R^2$, $R^3$ and $R^4$ are the same or different lower-alkyl;
n is zero or one;
$R^5$ is hydrogen, lower-alkyl, $C_3$–$C_7$-monocyclic cycloalkyl, lower-alkoxy, phenyl, phenyl-lower-alkyl, phenyl-lower-alkyl in which the phenyl ring is substituted in the 2, 3, or 4-position by one to two, the same or different, halogen substituents, or $R^5$ is a 5-membered aromatic monocyclic heterocycle selected from the group consisting of thienyl, furanyl and isoxazolyl; and $R^6$ is hydrogen or lower-alkyl; or when n is zero, $R^5$ and $R^6$ together are $—(CH_2)_m—$ wherein m is an integer from four to six; or a pharmaceutically acceptable acid-addition salt thereof, together with a pharmaceutically acceptable carrier, adjuvant, diluent or vehicle; with the proviso that when $R^1$, $R^2$, $R^3$ and $R^4$ are methyl, n is zero and $R^6$ is hydrogen or methyl, $R^5$ cannot be hydrogen; further provided that when n is zero, $R^5$ cannot be lower-alkoxy, phenyl, or a 5-membered aromatic monocyclic heterocycle.

12. A pharmaceutical composition according to claim 11 wherein $R^1$, $R^2$, $R^3$ and $R^4$ are methyl; n is one; $R^5$ is lower-alkoxy, 3,4-dichlorophenyl-lower-alkyl, or thienyl; and $R^6$ is hydrogen or methyl.

13. A pharmaceutical composition according to claim 12 wherein the compound is 3,4-dichloro-N-methyl-N-[2-(1,2,3,4-tetramethyl-3-piperidinyl)ethyl]benzeneacetamide or an acid addition salt thereof.

14. A method for the treatment of psychosis which comprises administering to a patient in need of such treatment an effective amount of a compound of the formula:

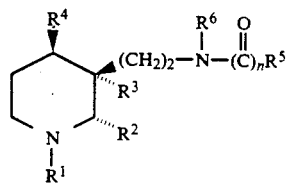

wherein:
$R^1$ is lower-alkyl, or phenyl-lower-alkyl;
$R^2$, $R^3$ and $R^4$ are the same or different lower-alkyl;
n is zero or one;
$R^5$ is hydrogen, lower-alkyl, $C_3$–$C_7$-monocyclic cycloalkyl, lower-alkoxy, phenyl, phenyl-lower-alkyl, phenyl-lower-alkyl in which the phenyl ring is substituted in the 3, 3, or 4-position by one to two, the same or different, halogen substituents, or $R^5$ is a 5-membered aromatic monocyclic heterocycle selected from the group consisting of thienyl, furanyl and isoxazolyl; and
$R^6$ is hydrogen or lower-alkyl; or when n is zero, $R^5$ and $R^6$ together are $—(CH_2)_m—$ wherein m is an integer from four to six; or a pharmaceutically acceptable acid-addition salt thereof; with the proviso that when $R^1$, $R^2$, $R^3$ and $R^4$ are methyl, n is zero and $R^6$ is hydrogen or methyl, $R^5$ cannot be hydrogen; further provided that when n is zero, $R^5$ cannot be lower-alkoxy, phenyl, or a 5-membered aromatic monocyclic heterocycle.

15. A method according to claim 14 wherein $R^1$, $R^2$, $R^3$ and $R^4$ are methyl; n is one; $R^5$ is lower-alkoxy, 3,4-dichlorophenyl-lower-alkyl, or thienyl; and $R^6$ is hydrogen or methyl.

16. A method according to claim 15 wherein the compound is 3,4-dichloro-N-methyl-N-[2-(1,2,3,4-tetramethyl-3-piperidinyl)-ethyl]benzeneacetamide, or an acid-addition salt thereof.

* * * * *